United States Patent [19]

Nowakowsky et al.

[11] Patent Number: 4,873,299

[45] Date of Patent: Oct. 10, 1989

[54] BATCHWISE PREPARATION OF CROSSLINKED, FINELY DIVIDED POLYMERS

[75] Inventors: Bernhard H. Nowakowsky, Ludwigshafen; Juergen Beck, Mannheim; Heinrich Hartmann, Limburgerhof; Christos Vamvakaris, Kallstadt, all of Fed. Rep. of Germany

[73] Assignee: BASF Aktiengesellschaft, Ludwigshafen, Fed. Rep. of Germany

[21] Appl. No.: 28,449

[22] Filed: Mar. 20, 1987

[30] Foreign Application Priority Data

Mar. 21, 1986 [DE] Fed. Rep. of Germany ....... 3609545

[51] Int. Cl.$^4$ ................................................ C08F 2/18
[52] U.S. Cl. ...................................... 526/73; 526/264; 526/318.2
[58] Field of Search ............................... 526/73, 307.7

[56] References Cited

U.S. PATENT DOCUMENTS 4,286,082  8/1981  Tsubakimoto .................... 526/240
4,351,922  9/1982  Yoshida ............................ 525/116

*Primary Examiner*—Christopher Henderson
*Attorney, Agent, or Firm*—Bill C. Panagos

[57] ABSTRACT

Crosslinked, finely divided, water-absorbing polymers are prepared in a batchwise process by copolymerization of 100 parts by weight of a monomer mixture of acrylic acid or methacrylic acid, each of which is neutralized with from 0 to 100 mol% of an alkali metal or ammonium base,or acrylamide, methacrylamide or N-vinylpyrrolidone with, as a crosslinking agent, from 0.01 to 5 parts by weight of a monomer containing two or more ethylenically unsaturated double bonds in 20–80% by weight aqueous solution in the presence of an initiator in a multistage procedure in a batchwise mixing apparatus with constant thorough mixing in all stages, in the first stage the aqueous monomer solution being copolymerized at from 45° to 95° C. and under from 0.1 to 0.8 bar with removal of some of the water by distillation, in the second stage the copolymerization being completed at from 100° to 170° C. under a pressure of up to 8 bar, and in the third stage the water content of the resulting finely divided copolymer being decreased to 0.5–10% by weight under reduced pressure.

4 Claims, No Drawings

BATCHWISE PREPARATION OF CROSSLINKED, FINELY DIVIDED POLYMERS

German Laid-Open Application DOS 3,432,690 discloses a process for the continuous preparation of crosslinked polymers, in which water-soluble monomers are polymerized in the presence of a crosslinking agent and of initiators in a kettle which is equipped with a plurality of mutually parallel rotating stirrer shafts provided with stirrer blades. The polymerization is carried out continuously in a two-arm kneader or, for example, in a three-shaft kneader. The polymerization temperature is preferably from 70 to 100° C. In this type of reactor, a high degree of back-mixing takes place, so that the monomer solution is introduced onto the finely divided water-containing gel polymer and polymerization of the monomer takes place on the surface of the polymer gel. The finely divided polymer gels prepared in this manner have a relatively high residual monomer content and contain substantial amounts of extractables, i.e. soluble components. They therefore have to be subjected, in a separate process step, to after-polymerization and subsequent crosslinking.

It is an object of the present invention to provide a process for the preparation of crosslinked, finely divided, water-absorbing polymers, in which the polymers obtained have a low residual monomer content and small amounts of extractables.

We have found that this object is achieved, according to the invention, by a process for the batchwise preparation of crosslinked, finely divided, water-absorbing polymers by copolymerization of 100 parts by weight of a monomer from group (a) or of a monomer mixture from groups
  (a) 50–100 parts by weight of acrylic acid or methacrylic acid, each of which has been neutralized with from
    0 to 100 mol % of an alkali metal or ammonium base, acrylamide, methacrylamide and N-vinylpyrrolidone, (b) 0–30 parts by weight of other water-soluble monoethylenically unsaturated monomers and
  (c) 0–20 parts by weight of water-insoluble monoethylenically unsaturated monomers
with from 0.01 to 5 parts by weight of, as a crosslinking agent, a monomer containing two or more ethylenically unsaturated double bonds, in 20–80% by weight aqueous solution in the presence of an initiator at above 45° C., if the copolymerization is carried out in several stages in a batchwise mixing apparatus with constant thorough mixing during all stages, in the first stage the aqueous monomer solution being copolymerized at from 45° to 95° C. under from 0.1 to 0.8 bar with removal of some of the water by distillation, in the second stage the copolymerization being completed at from 100° to 170° C. under a pressure up to 8 bar and, in the third stage, after the pressure has been let down, the water content of the resulting finely divided copolymer being reduced to 0.5–10% by weight under reduced pressure at from 70° to 180° C. or under atmospheric pressure at from 120° to 180° C. The copolymerization is preferably carried out in a batchwise kneader having a selfpurging effect of not less than 80%.

Water-absorbing copolymers based on polymers of acrylic acid, methacrylic acid and their amides and on N-vinylpyrrolidone are prepared by copolymerizatioh of the monomers together with a crosslinking agent. Suitable monomers of group (a) are acrylic acid and/or methacrylic acid, each of which is neutralized with from 0 to 100 mol % of an alkali metal or ammonium base. This group of monomers also includes acrylamide, methacrylamide and N-vinylpyrrolidone. For the partial or complete neutralization of the acrylic acid or methacrylic acid, sodium hydroxide solution and/or potassium hydroxide solution are preferably used. Neutralization can of course also be carried out using sodium carbonate, potassium carbonate, ammonia or a substituted amine, such as trimethylamine, tri-n-octylamine or triethanolamine. Where acrylic acid or methacrylic acid is used for the polymerization, neutralization may be effected before, during or after the polymerization. In the copolymerization with the cross-linking agents, he monomers of group (a) can be used either alone or as a mixture with one another in any ratio. For example, acrylic acid alone or mixtures of acrylic acid and methacrylic acid or of acrylic acid and acrylamide or of acrylic acid, acrylamide and methacrylamide or mixtures of acrylamide and N-vinylpyrrolidone may be subjected to copolymerization. However, acrylic acid which has been neutralized with from 50 to 100 mol % of sodium hydroxide solution and/or potassium hydroxide solution is preferably used as the monomer of group (a). Neutralization of the acrylic acid is preferably effected before the polymerization or during the first stage of the polymerization. The monomers of group (a) can be copolymerized with the crosslinking agent either alone or as a mixture with the monomers of groups (b) and (c). In the case of mixtures of monomers from groups (a) to (c), the amount of monomers of group (a) is from 50 to 99%.

The monomers of group (b) consist of other water-soluble, monoethylenically unsaturated monomers which differ from the monomers of group (a). These include, for example, maleic acid, fumaric acid, crotonic acid, itaconic acid, vinylsulfonic acid, vinylpyridinium salts, N-vinylformamide, basic acrylates and methacrylates in the form of the salts with strong mineral acids or in quaternized form, eg. dimethylaminoethyl acrylate, diethylaminoethyl acrylate, dimethylaminopropyl acrylate, dimethylaminobutyl acrylate, diethylaminoethyl methacrylate, dimethylaminoethyl methacrylate and dimethylaminopropyl acrylate. This group of monomers also includes the hydroxyalkyl acrylates and hydroxyalkyl methacrylates, eg. hydroxyethyl acrylate, hydroxyethyl methacrylate, hydroxypropyl acrylates, hydroxypropyl methacrylates, hydroxybutyl acrylates and hydroxybutyl methacrylates, as well as acrylates and methacrylates which were obtained by esterification of polyethylene glycols with acrylic acid or methacrylic acid in a molar ratio of 1:1. The polyethylene glycols used for the esterification have molecular weights of from 126 to 8,500. From 0 to 30, preferably from 0.5 to 15, parts by weight of the monomers of group (b) are used per 100 parts by weight of the monomers of group (a).

The monomers of group (c) include water-insoluble monoethylenically unsaturated monomers. These are, for example, the esters of acrylic acid or methacrylic acid with monohydric alcohols of 1 to 18 carbon atoms, eg. methyl acrylate, ethyl acrylate, propyl acrylate, isopropyl acrylate, n-butyl acrylate, isobutyl acrylate, hexyl acrylate, 2-ethylhexyl acrylate, stearyl acrylate, the corresponding esters of methacrylic acid, diethyl fumarate, diethyl maleate, dimethyl maleate, dibutyl maleate, acrylonitrile, methacrylonitrile, vinyl acetate and vinyl propionate. From 0 to 20, preferably from 0.5 to 5, parts by weight of the monomers of group (c) are used per 100 parts by weight of the monomers of group (a) in the copolymerization.

The crosslinking agents used are compounds which contain two or more ethylenically unsaturated double bonds. Examples of suitable crosslinking agents are N,N'-methylenebisacrylamide, polyethylene glycol diacrylates and polyethylene glycol dimethacrylates, each of which is derived from a polyethylene glycol with a molecular weight of from 126 to 8,500, trimethylolpropane triacrylate, trimethylolpropane trimethacrylate, butanediol diacrylate, hexanediol diacrylate, hexanediol dimethacrylate, diacrylates and dimethacrylates of block copolymers of ethylene oxide and propylene oxide, adducts of ethylene oxide and/or propylene oxide with trimethyloloropane which have been diesterified or triesterified with acrylic acid or methacrylic acid, glycerol or pentaerythritol which have been diesterified or polyesterified with acrylic acid or methacrylic acid, triallylamine, tetraallylethylenediamine, divinylbenzene, diallyl phthalate, polyethylene glycol divinyl ether, trimethylolpropane diallyl ether, polyethylene glycol divinyl ether, butanediol divinyl ether, polyethylene glycol diallyl ether, butanediol diallyl ether and divinylethylene urea. The crosslinking agents are used in the copolymerization in an amount of from 0.01 to 5, preferably from 0.1 to 3, parts by weight per 100 parts by weight of the monomers of groups (a) to (c).

The monomers are polymerized in aqueous solution. The water-insoluble monomers, which may or may not be present, are usually finely dispersed in the aqueous solution with the aid of emulsifiers. Examples of suitable emulsifiers are oxyethylated nonylphenols, oxyethylated castor oil, alkylsulfates, sorbitan fatty acid esters, oxyethylated sorbitols, oxyethylated sorbitan fatty acid esters and alkylsulfonates. The emulsifiers are used in an amount of from 0 to 3 parts by weight per 100 parts by weight of the monomers of groups (a) to (c). The concentration of the aqueous monomer solution is preferably from 30 to 50% by weight.

Suitable initiators are, in the main, watersoluble compounds which form free radicals, for example azo initiators, such as 2,2'-azobis-(N,N'-dimethyleneisobutyramidine) dihydrochloride, 2,2'-azobis-(2-amidinopropane) dihydrochloride, 2,2'-azobis-(N,N'-dimethyleneisobutyramidine), 4,4'-azobis-(4-cyanopentanecarboxylic acid) and 2-carbamylazoisobutyronitrile, and dibenzoyl peroxide, dilauryl peroxide, di-2-ethylhexyl peroxydicarbonate, dicyclohexyl peroxydicarbonate, bis-(4-tertbutylcyclohexyl) peroxydicarbonate, tert-butyl perpivalate, tert-butyl perbenzoate, tert-butyl permaleate, di-tert-butyl peroxide, tert-butyl hydroperoxide, hydrogen peroxide, ammonium persulfate, potassium persulfate, sodium persulfate and redox catalysts, suitable reducing components being iron(II) ammonium sulfate, ascorbic acid, sodium hydroxymethanesulfinate, disodium disulfite and sodium bisulfite. The initiators can be used either alone or as a mixture. The rate of decomposition of the peroxides, which undergo rapid decomposition, can be reduced by the concomitant use of organic metal complexes, eg. copper acetylacetonate, so that the rate of decomposition of the peroxides can be adapted to the particular polymerization temperature chosen. Redox catalysts consisting of one or more peroxides and of a reducing agent are preferably used, a persulfate or perester or a mixture of a persulfate and a perester particularly preferably being used as a component of redox polymerization initiators. The polymerization initiators are used in an amount of from 0.01 to 5, preferably from 0.2 to 3 % by weight, based on the monomers employed in the polymerization.

In order to regulate the molecular weight of the polymers, polymerization may also be carried out in the presence of a polymerization regulator, eg. mercaptoethanol, mercaptopropanol, thioglycollic acid, dodecylmercaptan, formic acid or a halohydrocarbon, such as bromomethane or carbon tetrachloride. The polymerization regulators are used in an amount of from 0 to 3% by weight, based on the monomers employed in the polymerization.

According to the invention, copolymerization of the aqueous solution of the monomers is carried out in several stages in a batchwise mixing apparatus with continuous thorough mixing of the substances during all stages. Since, in the course of the polymerization, the aqueous monomer solution is converted to a finely divided polymer via gel-like material, vigorous mixing must be ensured in all stages of the process. Examples of suitable batchwise mixing apparatuses are kneaders which have a self-purging effect of not less than 80%. The kneaders may have one or more screws. The copolymerization can also advantageously be carried out in a single-screw cylindrical mixer whose stirrer shaft has disk segments which, on the outer end, possess mixing bars in an arrangement such that intensive circulatory mixing of the substances introduced into the mixer is effected. The single-screw cylindrical mixer has a diameter/length ratio of from 2:1 to 20:1. The disk segments are arranged in the form of a propeller on the stirrer shaft. From 2 to 25 of these disk segments are distributed over the entire length of the stirrer shaft, a disk segment consisting of from 2 to 7 individual elements arranged in a propeller-like manner. The mixing elements located on the outer end of the disk segments transport the polymerizing mixture inside the mixing apparatus and at the same time prevent polymer gel from being deposited on the internal wall of the mixer, because the mixing elements run close to the internal wall of the cylindrical mixer. Examples of suitable mixing elements are mixing bars which pass close to the wall or ploughshare-like attachments. The mixer also contains built-in flanged counterhooks for removing the gel formed during the polymerization from the disk segments of the stirrer shaft and from the mixing bars. Such mixing apparatuses too have a self-purging effect of more than 80%. Suitable apparatuses having a high self-purging effect are known and are described in, for example, Chem.-Ing.-Techn. 57 (1985), 1005.

The apparatuses which are suitable for polymerization are charged with the aqueous monomer solution which may contain a dissolved or dispersed initiator, the charge occupying not more than 45, preferably from 20 to 35 % by volume of the said apparatuses. The polymerization apparatuses can, if required, be heated or cooled and are designed for operation under reduced and superatmospheric pressure.

In the first stage of the copolymerization, the aqueous monomer solution is copolymerized in the presence of a polymerization initiator at from 45° to 95° C. under from 0.1 to 0.8 bar with removal of some of the water by distillation. The water evaporated is removed from the mixer via a pressure-regulating apparatus. By distilling off the water under reduced pressure, it is possible to set the polymerization temperature exactly and to remove the heat of polymerization from the system in this manner. In the first stage of the polymerization, water is distilled off in an amount sufficient to give a polymer gel of about 30-90% strength by weight, which can be converted to a crumb-like gel as early as the end of the first stage. The duration of polymerization of the first stage is about 5-60 minutes.

In the second stage of the copolymerization, the temperature of the reaction mixture is increased to 100°-170° C., preferably 120°-140° C. This means that, because of the water content of the polymerizing mixture, the pressure in the apparatus increases to about 1-8, preferably 2-5, bar. The polymerization is completed in the second stage. In this stage of the process too, the reaction mixture must be thoroughly mixed and subjected to shearing. The heat treatment of the copolymer in the second stage lasts for about 10-100, preferably 15-50, minutes. After this treatment, the pressure is brought to atmospheric pressure.

In the third stage of the copolymerization, likewise under constant thorough mixing of the reaction mixture, which has become crumb-like, the water content of the resulting finely divided copolymer is reduced to 0.5-10, preferably 3-6, % by weight at from 70° to 180° C. and under reduced pressure. The pressure under which the copolymers are dried is of course temperature-dependent and is from 10 to 800 mbar. The duration of drying is about 10-100 minutes. The crosslinked copolymer can, however, also be dried under atmospheric pressure at from 120° to 180° C.

This procedure gives a free-flowing finely divided polymer which has very high water absorption and is used, for example, as a soil conditioner or as an absorbent in hygiene articles, for example diapers. In the Examples, parts and percentages are by weight, unless stated otherwise. Determination of the absorptivity of the polymers In the Examples, the absorptivity of each of the polymers prepared for physiological saline is given. This was determined by enclosing 0.2 g of each polymer in a teabag-like filter paper bag and immersing it for 10 minutes in 0.9% strength aqueous saline. After subtracting the amount absorbed by the empty bag, the absorptivity of the polymer was calculated in each case. Determination of soluble components The content of soluble components not bound in the polymer network was determined by swelling the polymer for 8 hours in water and measuring the carbon content of the aqueous solution.

EXAMPLE 1

A monomer solution which is at 20° C. and consists of 500 parts of acrylic acid, 6 parts of N,N'-methylenebisacrylamide and 120 parts of water is initially taken under nitrogen in a 6 l single-screw cylindrical mixer whose stirrer shaft possesses disk segments which have mixing bars on the outer end in an arrangement such that thorough circulatory mixing of the content is achieved, the charge occupying 35% of the mixer capacity. The mixer has a diameter/length ratio of 7:1 and is designed to operate under reduced and superatmospheric pressure. 8 disk segments are arranged 15 cm apart on each stirrer shaft of the mixer, a disk segment consisting of three individual elements. 150 parts of 50% strength aqueous sodium hydroxide solution are then added to the constantly and thoroughly stirred monomer solution in order to neutralize 27% of the acrylic acid. During the neutralization, the reaction mixture is cooled to 30° C. Thereafter, 5 parts of ammonium peroxydisulfate in 25 parts of water are mixed in. The stirrer shaft and housing of the single-screw mixer are heatable and are brought to 45° C., while the pressure inside the mixer is brought to 200 mbar. The polymerization reaction is then started by adding 1 part of sodium bisulfite in 10 parts of water. At the same time, 300 parts of a 50% strength aqueous potassium hydroxide solution are added in the course of 10 minutes. The temperature of the reaction mixture increases to 72° C. During the polymerization, 270 parts of water are distilled 25 minutes. In the second stage of the polymerization, the pressure is first equilibrated to 1 bar under a nitrogen atmosphere, the mixer is then closed so that it is pressure-tight, and the reaction mixture therein is heated to 135° C. This increases the pressure in the mixer to 4 bar. The reaction mixture is treated for 20 minutes at this temperature and under pressure, while stirring constantly and thoroughly. After the pressure has been brought to atmospheric pressure, the water content of the resulting copolymer is reduced to 2.8% in the third stage, under 50 mbar and at 140° C., with constant thorough mixing. The pressure is then brought to atmospheric pressure. A crosslinked, finely divided water-absorbing polymer can then be removed from the mixer. The mean particle diameter of the polymer is 3 mm. 1 g of the polymer absorbs 61 g of physiological saline. By swelling in water, it is possible to extract about 9% of soluble components.

EXAMPLE 2

In the mixer described in Example 1, in which the charge occupies 30% of the capacity, a solution of 300 parts of acrylic acid, 100 parts of acrylamide, 35 parts of N-vinylpyrrolidone and 5 parts of butanediol divinyl ether in 150 parts of water is partially neutralized with 220 parts of 50% aqueous potassium hydroxide solution under nitrogen and with continued stirring, the temperature being restricted to 30° C. by cooling. A solution of 5 parts of potassium peroxydisulfate in 150 parts of water is mixed in, the stirrer shaft and the housing of the single-screw mixer are heated to 45° C. and the internal pressure of the mixer set to 400 bar. Polymerization is initiated by adding 0.5 part of sodium hydroxymethanesulfinate in 5 parts of water. During the 15 minute polymerization, 120 g of 50% strength aqueous potassium hydroxide solution are added and 260 parts of water are removed. The temperature of the reaction mixture increases to 83° C. In the second stage, the pressure is equilibrated to 1 bar with nitrogen, the mixer is closed tightly and the reaction mixture is then heated to 120° C., the pressure in the mixer increasing to about 3 bar. The constantly stirred reaction mixture is aftertreated for 20 minutes under these conditions. Finally, in the third stage, the pressure is equilibrated to atmospheric pressure and then reduced to 30 mbar, and the resulting copolymer is dried at 150° C. with thorough stirring to give a fine crumb-like material. The mixer is brought to atmospheric pressure, after which a crosslinked, finely divided water-absorbing polymer having a mean particle diameter of 3 mm can be removed. 1 g of the polymer absorbs 54 g of physiological saline. By swelling in water, it is possible to separate off about 7% of soluble components.

EXAMPLE 3

In the single-shaft mixer described in Example 1, in which the charge occupies 40% of the capacity, a stirred solution of 250 parts of acrylic acid, 40 parts of methacrylic acid, 43 parts of itaconic acid, 7 parts of divinylbenzene and 7 parts of sodium pentadecylsulfonate in 250 parts of water is partially neutralized with 230 parts of 50% strength aqueous potassium hydroxide solution under nitrogen, and the temperature of the solution is kept at 30° C. during this procedure by removing heat. After the addition of a solution of 10 parts of sodium peroxydisulfate in 50 parts of water, the stirrer shaft and housing of the single-shaft mixer are heated to 45° C., the mixture is evacuated to 300 mbar and the polymerization is initiated by adding 0.5 parts of ascorbic acid in 30 parts of water. The reaction mixture reaches 72° C. during the 25 minute polymerization in this first stage. 230 parts of water are distilled off. For the second stage of the polymerization, the pressure is equilibrated to 1 bar with a nitrogen atmosphere, the mixer is closed so that it is pressure-tight and the reaction mixture is heated to 130° C., the pressure building up to about 3.5 bar. Aftertreatment is carried out at this temperature and under this pressure with thorough mixing for 35 minutes. Thereafter, the temperature is decreased to 60° C., the pressure is reduced to atmospheric pressure and subsequent neutralization is carried out with 120 parts of 50% strength aqueous potassium hydroxide solution with thorough mixing of the polymer. In the third stage, the pressure is reduced to 20 mbar and drying is carried out at 120° C. to a residual water content of 5.2% to give a finely divided solid having a mean particle diameter of 3 mm.

1 g of the resulting copolymer absorbs 58 g of physiological saline. By swelling in water, it is possible to extract about 7% of soluble components.

We claim:

1. A process for the batchwise preparation of a crosslinked, finely divided, Water-absorbing polymer, which comprises multistage copolymerization in a batchwise mixing apparatus, with constant thorough mixing in all stages, of 100 parts by weight of a monomer from group (a) or of a monomer mixture from groups (a) 50–100 parts by weight of acrylic acid or methacrylic acid, each of which has been neutralized with from 0 to 100 mol % of an alkali metal or ammonium base, acrylamide, methacrylamide and N-vinylpyrrolidone,
   (b) 0–30 parts by weight of other water-soluble monoethylenically unsaturated monomers and
   (c) 0–20 parts by weight of water-insoluble monoethylenically unsaturated monomers with from 0.01 to 5 parts by weight of, as a crosslinking agent, a monomer containing two or more ethylenically unsaturated double bonds, in 20–80% by weight aqueous solution in the presence of an initiator at above 45° C., in the first stage the aqueous monomer solution being copolymerized at from 45° to 95° C. under from 0.1 to 0.8 bar with removal of some of the water by distillation, in the second stage the copolymerization being completed at from 100° to 170° C. under a pressure up to 8 bar and, in the third stage, after the pressure has been let down, the water content of the resulting finely divided copolymer being reduced to 0.5–10% by weight under reduced pressure at from 70° to 180° C. or under atmospheric pressure at from 120° to 180° C.

2. A process as claimed in claim 1, wherein the batchwise mixing apparatus used is a kneader having a self-purging effect of not less than 80%.

3. A process as claimed in claim 1, wherein acrylic acid, which has been neutralized with from 10 to 100 mol % of sodium hydroxide solution and/or potassium hydroxide solution, is copolymerized with a monomer containing two or more ethylenically unsaturated double bonds.

4. A process as claimed in claim 1, wherein N,N' methylenebisacrylamide, polyethylene glycol diacrylates, polyethylene glycol divinyl ether, butanediol divinyl ether, trimethylolpropane triacrylate, butanediol diacrylate, polyethylene glycol diallyl ether and/or butanediol diallyl ether are used as crosslinking agents.

* * * * *